United States Patent [19]
Dietrich et al.

[11] 3,961,094
[45] June 1, 1976

[54] FLAVORING AGENTS COMPRISING UNSATURATED BUTYROLACTONE DERIVATIVES AND PRECURSORS THEREOF

[75] Inventors: Paul Dietrich; Erling Sundt, both of Geneva, Switzerland

[73] Assignee: Firmenich S.A., Geneva, Switzerland

[22] Filed: Jan. 22, 1975

[21] Appl. No.: 543,061

Related U.S. Application Data

[60] Division of Ser. No. 312,031, Dec. 4, 1972, Pat. No. 3,884,247, which is a division of Ser. No. 115,122, Feb. 12, 1971, abandoned, which is a continuation-in-part of Ser. No. 768,896, Oct. 18, 1968, abandoned.

[30] Foreign Application Priority Data

Oct. 18, 1967 Switzerland.................... 14559/67
Oct. 12, 1968 Switzerland.................... 15191/68

[52] U.S. Cl. ............................................. 426/536
[51] Int. Cl.$^2$ ......................................... A23L 1/226
[58] Field of Search ............ 426/65, 536; 260/343.6

[56] References Cited
UNITED STATES PATENTS

3,075,998    1/1963    Lardelli et al. .................. 260/343.6
3,530,149    9/1970    Fiecchi ............................ 426/65 X

FOREIGN PATENTS OR APPLICATIONS

6,517,153    7/1966    Netherlands

OTHER PUBLICATIONS

Pastureau, *Bull. Soc. Chemique France,* vol. 5 (1909), p. 227.
Monnin, *Helv. Chem. Acta,* vol. 40 (1957), pp. 1983–1989.
Wolff, *Lieb. Annalen Der Chemie,* vol. 317 (1901), pp. 1–6.
Fichter et al., *Berichte,* vol. 35 (1902), pp. 1626–1630.
Moncrieff, The Chemical Senses, Leonard Hill: London 1944, pp. 195–198.

*Primary Examiner*—Joseph M. Golian
*Attorney, Agent, or Firm*—Pennie & Edmonds

[57] ABSTRACT

This specification relates to the use of some substituted 2-hydroxy-2-buten-4,1-olides and acid precursors thereof as flavoring agents for foodstuffs, animal feeds and beverages. The specification also includes a method for preparing the said olides by heating said precursors and a method for the preparation of one of said precursors.

8 Claims, No Drawings

FLAVORING AGENTS COMPRISING UNSATURATED BUTYROLACTONE DERIVATIVES AND PRECURSORS THEREOF

CROSS REFERENCE TO RELATED APPLICATION

This application is a divisional of application Ser. No. 312,031, filed Dec. 4, 1972, which has since issued as U.S. Pat. No. 3,884,247 on May 20, 1975, and which is a divisional of application Ser. No. 115,122, filed Feb. 12, 1971, which in turn is a continuation-in-part of application Ser. No. 768,896, filed Oct. 18, 1968, of which the latter two applications have been abandoned.

BRIEF SUMMARY OF THE INVENTION

The present invention concerns the use of substituted unsaturated butyrolactone derivatives (also called 2-buten-4, 1-olides) and acid precursors thereof, of the formula

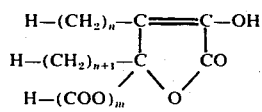

wherein $n$ and $m$ each can be O or 1, as flavoring agents.

It has been found that the lactones of Formula I, wherein $n$ is O or 1 and $m$ is O in either instance, possess valuable organoleptic properties and are useful for modifying the taste and flavor of foods, animal feeds, beverages, pharmaceutical preparations and tobacco smoke. They are also useful for the preparation of compounded mixtures used in flavoring the abovementioned goods. In particular, lactone I, wherein $n$ is 1 and $m$ is O, is capable of imparting to said mixtures a maple-like flavor while lactone I, wherein $n$ and $m$ are both O, is capable of imparting to said mixtures a "burnt sugar" — like flavor.

The acid precursor of the olide $n=1$, $m=O$ of Formula I is known and is represented by the formula

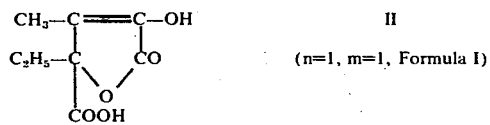

(see, for example, J. Food Sci. 32, 611 (1967) and Berichte 35, 1626 (1902).

The acid precursor of the olide $n=O$, $m=O$ of Formula I is known and is represented by the formula

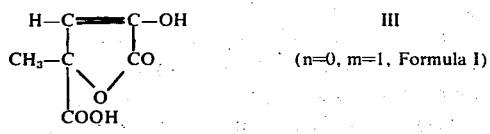

(see, for example, Lieb. Ann. 317, 1 (1901)).

The invention also relates to a process for the preparation of the above-defined olides I from their precursors II and III.

When heated, the acids of Formulas II and III can generate the said olides of Formula I. Thus the said acids represent also valuable additives for flavoring foods, animal feeds, beverages and tobacco since the flavor of the corresponding olides I is developed when the said foods, animal feeds or beverages containing the additives are heated or cooked or when tobacco smoke is evolved by burning tobacco containing the said additives.

DETAILED DESCRIPTION

The lactones I ($n=O$ or 1, $m=O$) are prepared by heating the acid precursors of Formulas II and III in order to form the lactones I by decarboxylation. The conversion of the acids II and III into the lactones I can be effected at temperatures exceeding 50°C. In order to accelerate the reaction rate it is advisable to use higher temperatures, for instance, at least 100°C. More preferably, the conversion of acids II and III into lactones I is effected at temperatures in the vicinity of the melting point of the precursor or at temperatures higher than the melting point. The heating period may vary from a few seconds, in case the conversion is effected at high temperature in a pyrolysis apparatus, to several hours, for instance, 24 hours at the lower temperatures. Long reaction times coupled with high temperatures should preferably be avoided since charring may then happen.

When the acid precursors II and III are used as flavor precursors in foods or beverages which, in the course of their manufacture, are subjected to a heat treatment such as boiling, cooking or baking, the conversion of II or III into lactones I will take place at the temperatures normally used for said heat treatments.

Acid II may be prepared by treating 2-ketobutyric acid by a strong acid, preferably a mineral or a mixed mineral-organic acid, according to the scheme underneath

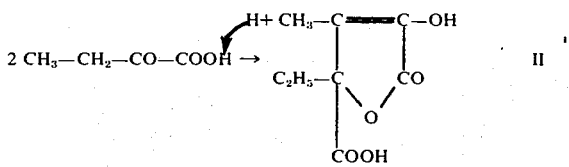

The strong mineral or mixed mineral-organic acids used in the process for preparing acid II can be, for instance, hydrogen chloride, perchloric acid, phosphoric acid, sulphuric acid, trifluoracetic acid or p-toluene sulfonic acid. It is particularly convenient to use dry gaseous hydrogen chloride and to operate at room temperature in benzene solution although other temperatures such as those comprised between 0° and 80° or higher and other common organic solvents such as tetrahydrofuran, dioxan, toluene or chloroform may also be used.

The acid of Formula III can result from the dimerization of pyruvic acid according to methods described in the literature. (See, for example, Lieb. Ann. 317, 1 (1901).) The dimerization can be acid self-catalyzed or catalyzed by the addition of stronger acids such as HCl or $H_2SO_4$. The dimerization can also be catalyzed by bases, such as for instance, KCN, KOH, Ba(OH)$_2$, NH$_4$OH, etc. (See Lieb. Ann. 305, 155 (1899).) In such cases where basic catalysis is employed, the desired acid can be liberated from the reaction mixture by acidifying the said mixture according to usual means. Until now, the structure of acid III was not known with certainty and the three formulas shown below have been proposed although Formula III c was strongly favored. (See above references.)

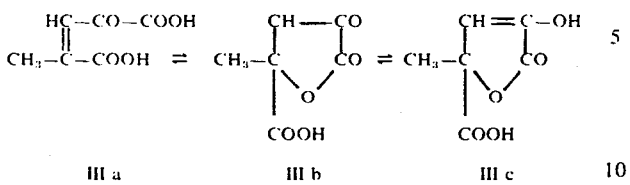

Spectral measurements which shall be described in detail hereinafter have now shown the IIIC is the correct structure.

At an appropriate dilution, the lactones I ($n=0$ or 1, $m=0$) develop in foods, beverages and other edible materials a flavor and an odor resembling those of maple, malt, molasses, fenugreek and caramel. The addition of 2-hydroxy-3-methyl-4-ethyl-2-buten-4,1-olide to foods and beverages allows reproducing rather accurately the flavor and the taste of maple. 2-hydroxy-4-methyl-2-buten-4,1-olide due to its intense "burnt sugar" note is particularly suited for modifying or enhancing flavors such as caramel, roasted nuts and hazelnuts, chocolate and kola. In foods and beverages, quantities of 0.1 to 50 ppm by weight of food or beverage are in most cases sufficient to produce a marked effect. Thus, cakes, syrups, cooked sugar, ice-creams and soft drinks can be perfumed and flavored. With tobacco, slightly higher dosages may be required, for instance, of the order of 5 to 20 g. per 100 kg. of tobacco.

Acid II and III can be used as additives to flavor foods which are normally subjected to a heat treatment such as boiling, cooking or baking. Such food products comprise for instance casserole dishes, pies, cakes, pastry and confectionery. The flavor is then developed when the food product containing the additive is heat processed. As a result, flavoring effects comparable to those obtained with the corresponding lactones can be obtained when similar quantities of acids II and/or III are added to edible goods or tobacco.

Acid II, mixed to tobacco, imparts to the smoke thereof a very pleasant maple perfume when the tobacco is burned.

The olides I can also be used in admixture with other flavoring agents when specific flavoring effects are desired.

The following Examples illustrate the preparation and the use of compounds I, II and III in a more detailed manner. In the Examples, temperatures are given in degrees Centigrade.

EXAMPLE 1

Preparation of
2-hydroxy-3-methyl-4-ethyl-4-carboxy-2-buten-4,1-olide

Dry hydrogen chloride (135 g.) was introduced at 20° in the course of 7 hours into 1387.7 g of α-ketobutyric acid dissolved in benzene (1338 g.). The mixture was allowed to stand overnight at room temperature. Crystals which formed were collected by suction-filtration and the water which was present in the benzene mother-liquors was removed by decantation. After several hours, a new crop of crystals formed in the benzene solution and was collected. The total yield of 2-hydroxy-b 3-methyl-4-ethyl-4-carboxy-2-buten-4,1-olide was 1166.5 g., m.p. 152°–154° (with decomposition).

EXAMPLE 2

Preparation of
2-hydroxy-3-methyl-4-ethyl-2-buten-4,1-olide 2-hydroxy-3-methyl-4-ethyl-4-carboxy-2-buten-4,1-olide (186 g.) was heated at 160° until the evolution of $CO_2$ had ceased. The reaction product was distilled and furnished 130.7 g. of lactone, b.p. 70°–71°/0.003 Torr, m.p. 21°.

EXAMPLE 3

Preparation of 2-hydroxy-4-methyl-2-buten-4,1-olide 2-hydroxy-4-methyl-4-carboxy-2-buten-4,1-olide was prepared according to the methods described in the literature (see, for instance, Lieb. Ann. 317, 1 (1901); 305, 155 (1899)) and had the following constants: m.p. 116°–118° C. (uncorrected); NMR spectrum ($CCl_4$ -deuterated acetone) 1.65 (s, $CH_3$); 2.40 (s, H vinyl); 6.15 (H enol); 8.32 (H carboxyl) δ ppm.

A 10% solution of the above olide in diglyme (diethylene glycol dimethoxyether) was flash-pyrolyzed as follows: the solution was introduced dropwise in a pyrolysis apparatus of the type described in Chem. Ber. 93, 2677 (1960). The operation was performed under about 10 Torr of nitrogen and the pyrolysis column was kept at 300°–350°C. The mixture of pyrolysis product and solvent was collected in a trap at −20°C. The condensate was fractionated under reduced pressure and gave pure 2-hydroxy-4-methyl-2-buten-4,1-olide the properties of which were similar to those reported in the literature (Bull. Soc. Chim. France (4) 5, 227 (1909)).

EXAMPLE 4

Caramel flavor composition

An imitation caramel flavor composition was prepared by mixing the following ingredients (parts by weight).

| Ingredient | Amount |
|---|---|
| Ethyl vanillin | 50 |
| Maltol | 30 |
| 6-Methylcoumarin | 10 |
| Dihydrobenzopyrone | 70 |
| Diacetyl | 50 |
| Acetylpropionyl | 10 |
| Ethyl lactate | 770 |
| Total | 990 |

2-hydroxy-4-methyl-2-buten-4,1-olide (10 g.) was added to 990 g. of the above mixture which was then called the "test composition". Ethyl lactate (10 g.) was added to 990 g. of the said above mixture which was then called the "control composition".

Ice-cream was prepared from 1 liter milk, 5 egg yolks and 250 g. of sugar as follows. The milk was heated. The sugar was mixed with the egg yolks and the heated milk added, while stirring until the mass was smooth and progressively thickened.

Then the test composition and the control composition were added to 2 portions of ice-cream in the ratio of 100 mg. per 1 kg. of mass. The masses were frozen and processed in the conventional manner.

The finished ice-cream samples were tasted by a panel of several trained persons who had to express their opinion about the flavor of the samples. All members of the panel declared with no hesitation that the test ice-cream was more nutty, less buttery, had more depth and a more burnt caramel character than the control and that its taste was far more pleasant.

EXAMPLE 5

Maple flavor composition

An artificial maple flavor composition was prepared by mixing the following ingredients (parts by weight).

| Fenugreen Extract | 200 |
| Ethyl vanillin | 20 |
| Methylcyclopentanolone | 10 |
| Propylene glycol | 750 |
| Total | 980 |

2-hydroxy-3-methyl-4-ethyl-2-buten-4,1-olide (20 g.) was added to 980 g. of the above mixture which was then called the "test composition". Propylene glycol (20 g.) was added to 980 g. of the above mixture which was then called the "control composition".

The test and control compositions were added to two portions of syrup (prepared by dissolving 6.5 kg. of sucrose into 3.8 liters of warm water, boiling 2 minutes and allowing the liquid to cool) in a proportion of 100 mg./1 kg. of syrup.

The finished syrup samples were tasted on hot waffles by a panel of persons in a manner analogous to that described in Example 4. The syrup containing the test composition was judged to be more typical than the control sample and to have a more complete, more rounded and more natural note.

EXAMPLE 6

Flavoring composition

A flavoring composition was prepared by mixing together the following ingredients (gram).

| 2-hydroxy-3-methyl-4-ethyl-2-buten-4,1-oxide | 1 |
| Vanillin | 9 |
| Solid Coffee Extract | 30 |
| Solid Liquorice Extract | 30 |
| Solid Horehound Extract | 5 |
| Propylene glycol | 460 |
| Water | 465 |
| | 1000 g. |

The above composition was used to flavor foods and beverages, the preparation of which is described hereinafter in the proportions shown for 100 kg. of material to be flavored.

| Syrup | 100 g. |
| Cooked sugar | 150 g. |
| Ice-cream | 100 g. |
| Cake | 200 g. |
| Pudding | 80 g. |

Syrup: 1 kg. of sucrose was dissolved by heating in 600 ml. of water. The syrup was filtered and allowed to cool.

Cooked sugar: 100 ml. of syrup and 20 g. of glucose were mixed together and slowly heated to 145°C. The flavor was added and the mass was allowed to harden by cooling.

Ice-cream: The ice-cream was prepared as described in Example 4.

Cake: The following ingredients were mixed together with 100 g. of vegetable margarine, 1.5 g. sodium chloride, 100 g. sucrose, 2 eggs and 100 g. of flour. The flavor was added to the mass. The cake was cooked 40 minutes at 180°C.

Pudding: To 500 ml. of warmed milk were added with stirring a mixture of 60 g. of sucrose and 3 g. of pectin. The mixture was boiled for a few seconds and the flavor was added. The mixture was allowed to cool.

EXAMPLE 7

Flavoring of tobacco

A blend of pipe tobacco was prepared by mixing the following grades of tobacco (parts by weight).

| U.S.A. Flue cured Virginia, first quality grade | 20 |
| India Flue cured Virginia, medium grade | 35 |
| Pakistan Flue cured Virginia, lower grade | 30 |
| Southern China Flue cured Virginia | 5 |
| Syria Fire cured Latakia | 8 |
| Perique | 2 |

A hundred kilograms of the above blend were sprayed with 2 kg. of a 1% solution of 2-hydroxy-4-methyl-2-buten-4,1-olide in a 1:1 mixture of ethanol and propylene glycol. The treated tobacco was allowed to stand until it was dry enough to be tested. The treated tobacco was compared to a batch of untreated tobacco of the same blend by a panel of experienced tobacco testers. All members of the panel declared with no hesitation that the treated tobacco gave a more pleasant smoke than the untreated tobacco, with a distinct maple-like flavor.

What we claim is:

1. A product selected from among heatable and non-heatable foodstuffs, animal feeds and beverages containing at least one compound of the formula $$\begin{array}{c} H-(CH_2)_n-C=\!=\!=C-OH \\ H-C \quad\quad CO \\ H-(CH_2)_{n+1} \quad O \end{array}$$

or from heatable foodstuffs, animal feeds and beverages containing at least one compound of the formula $$\begin{array}{c} H-(CH_2)_n-C=\!=\!=C-OH \\ H-(CH_2)_{n+1}-C \quad\quad CO \\ HOOC \quad O \end{array}$$

wherein $n$ can be 0 or 1, said compound being present in an amount of between 0.1 and 50 parts per million by weight.

2. The product of claim 1 wherein said compound is 2-hydroxy-4-methyl-2-buten-4,1-olide.

3. The product of claim 1 wherein said compound is 2-hydroxy-3-methyl-4-ethyl-2-buten-4,1-olide.

4. The product of claim 1 wherein said compound is 2-hydroxy-4-methyl-4-carboxy-2-buten-4,1-olide.

5. The product of claim 1 wherein said compound is 2-hydroxy-3-methyl-4-ethyl-4-carboxy-2-buten-4,1-olide.

6. A product selected from among heatable type foodstuffs, animal feeds and beverages having added thereto from between 0.1 to 50 parts per million by weight of at least one compound of the formula

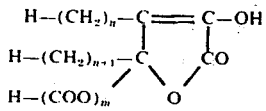

wherein $n$ and $m$ each can be 0 or 1.

7. A process for modifying, imparting or enhancing the maple, caramel, roasted nuts and hazelnuts character of the flavor of heatable and non-heatable foodstuffs, animal feeds and beverages, which comprises adding thereto at least one compound of the formula

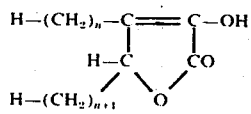

or for similarly effecting the flavor of heatable foodstuffs, animal feeds and beverages by adding thereto at least one compound of the formula

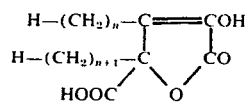

wherein $n$ can be 0 or 1, and the amount of compounds added is between 0.1 and 50 parts per million by weight.

8. A process for modifying, imparting or enhancing the maple, caramel, roasted nuts and hazelnuts character of the flavor of heatable foodstuffs, animal feeds and beverages, which comprises adding thereto at least a quantity of 0.1 to 50 parts per million by weight of at least one compound of the formula

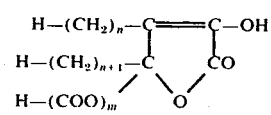

wherein $n$ and $m$ each can be 0 or 1.

* * * * *

UNITED STATES PATENT AND TRADEMARK OFFICE
CERTIFICATE OF CORRECTION

PATENT NO. : 3,961,094
DATED : June 1, 1976
INVENTOR(S) : Paul Dietrich et al.

It is certified that error appears in the above–identified patent and that said Letters Patent are hereby corrected as shown below:

Column 3, line 68 "2-hydroxy-b 3-methyl..." should be -- 2-hydroxy-3-methyl...--

Column 5, line 44 "2-buten-4,1-oxide" should be -- 2-buten-4,1-olide--

Signed and Sealed this

Twenty-first Day of September 1976

[SEAL]

Attest:

RUTH C. MASON
*Attesting Officer*

C. MARSHALL DANN
*Commissioner of Patents and Trademarks*